United States Patent [19]

Ishibashi

[11] Patent Number: 5,518,933
[45] Date of Patent: May 21, 1996

[54] METHOD OF ANALYZING WASHINGS FOR FREE ACIDS AND IONS

[75] Inventor: Tadaya Ishibashi, Amagasaki, Japan

[73] Assignee: Unitika Ltd., Hyogo, Japan

[21] Appl. No.: 358,236

[22] Filed: Dec. 16, 1994

Related U.S. Application Data

[63] Continuation-in-part of Ser. No. 81,856, Jun. 23, 1993, abandoned, which is a continuation of Ser. No. 806,823, Dec. 6, 1991, abandoned, which is a continuation of Ser. No. 485,252, Feb. 26, 1990, abandoned.

[30] Foreign Application Priority Data

Mar. 10, 1989 [JP] Japan .................................... 1-59075

[51] Int. Cl.⁶ .................................................. G01N 31/16
[52] U.S. Cl. ............... 436/163; 436/147; 436/150; 436/151; 324/439; 324/441; 73/61.46; 205/788.5
[58] Field of Search .......................... 436/163, 147, 436/150, 151; 422/82.02; 324/439, 441, 693, 425; 73/61.43, 61.46, 61.59; 204/405, 406, 408, 412, 416, 153.23

[56] References Cited

U.S. PATENT DOCUMENTS

| | | | |
|---|---|---|---|
| 3,531,252 | 9/1970 | Rivers et al. | 436/100 |
| 3,593,119 | 7/1971 | Brum et al. | 324/439 |
| 3,649,205 | 3/1972 | Shirakawa et al. | 422/62 |
| 3,716,333 | 2/1973 | Peuschel et al. | 436/79 |
| 3,870,466 | 3/1975 | Rellstab et al. | 436/51 |
| 4,002,428 | 1/1977 | Blanchard | 436/150 |
| 4,018,565 | 4/1977 | Fletcher et al. | 463/51 |
| 4,026,665 | 5/1977 | Mansfield et al. | 436/123 |
| 4,104,028 | 8/1978 | Howarth | 436/147 |
| 4,199,323 | 4/1980 | Miller, Jr. et al. | 436/150 |
| 4,230,554 | 10/1980 | Blanke | 204/405 |
| 4,822,456 | 4/1989 | Bryan | 204/153.1 |
| 4,886,590 | 12/1989 | Tittle | 204/232 |
| 4,907,453 | 3/1990 | Marlow et al. | 73/584 |
| 4,950,610 | 8/1990 | Tittle | 436/164 |

FOREIGN PATENT DOCUMENTS

| | | |
|---|---|---|
| WO88/04962 | 7/1988 | European Pat. Off. |
| 44-31074 | 12/1969 | Japan |
| 51-51996 | 5/1976 | Japan |
| 55-1588 | 1/1980 | Japan |
| 57-029946 | 2/1982 | Japan |
| 62-2144 | 6/1987 | Japan |

OTHER PUBLICATIONS

JP 62-2144 (abstract)—World Patent Index, accession No. 87-045677.
Y. Oguri et al., "A new computerized analyzing method of acid and cation concentration in hydrofluoric-nitric acid bath", Chemical Abstracts, vol. 104, No. 26, p. 784, Reference No. 104:236424H, Jun. 30, 1986.
I. Kotani, "Handy method for determining the concentrations of the metal ions and acid in pickling solutions", Chemical Abstracts, vol. 99, No. 26, pp. 762–763, Reference No. 99:2242850, Dec. 26, 1990.

Primary Examiner—Jill Warden
Assistant Examiner—Maureen M. Wallenhorst
Attorney, Agent, or Firm—Barnes, Kisselle, Raisch, Choate, Whittemore & Hulbert

[57] ABSTRACT

A method of determining the concentrations of at least two of plural kinds of known free acids and ions contained in a solution, wherein these known free acids and ions are known beforehand to be different from each other in temperature changes and conductivity changes which are to occur in response to a titrant. The method includes a step of generating a differential temperature curve and an electric conductivity curve, which are obtained from a thermometric titration and a conductometric titration respectively and are used complementarily so that an end point which is hardly ascertained by one method of titration may be ascertained by the other method.

4 Claims, 6 Drawing Sheets

METHOD OF ANALYZING WASHINGS FOR FREE ACIDS AND IONS

This is a continuation-in-part of the U.S. application Ser. No. 08/081,856 filed on Jun. 23, 1993 now abandoned which is a continuation of U.S. application Ser. No. 07/806,823 filed on Dec. 6, 1991 now abandoned which is a continuation of U.S. application Ser. No. 07/485,252 filed on Feb. 26, 1990 now abandoned which takes priority from Japanese Application Serial Number 1-59075 filed on Mar. 10, 1989.

FIELD OF THE INVENTION

The present invention relates to a method of analyzing a solution, said solution being known beforehand to contain plural kinds of free acids and ions different from each other in temperature changes and conductivity changes which are to occur in response to a titrant, and more particularly to a method of analyzing a solution containing a strong acid, a weak acid, ferric ions ($Fe^{3+}$) and ferrous ions ($Fe^{2+}$) which are known beforehand to allow end points to appear in this order when the solution is subjected to a titration.

Figure 10:
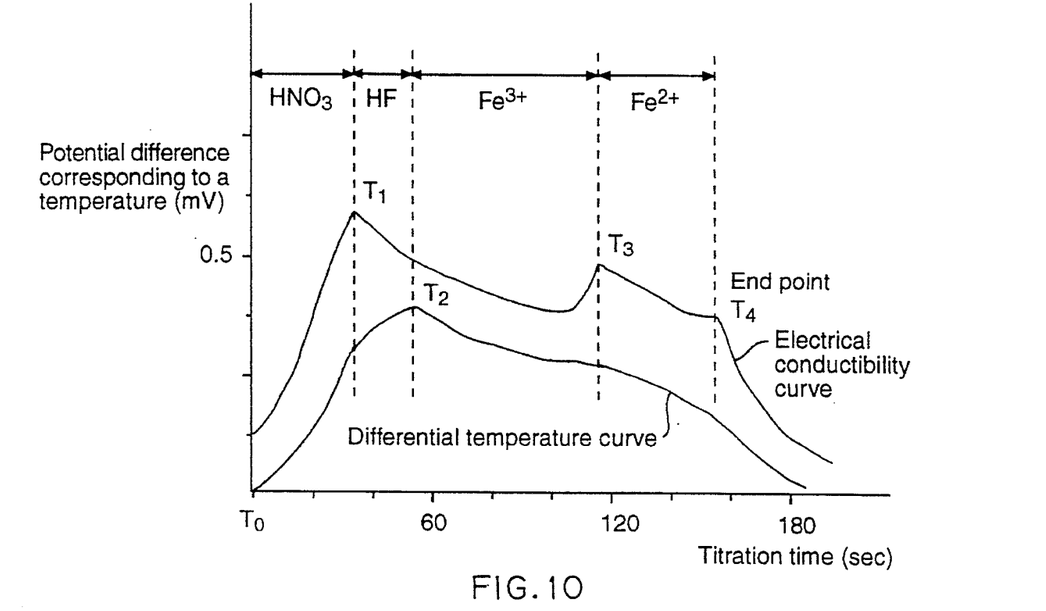
FIGS. 10 and 11 illustrate two curves, respectively depicting the results of a thermometric titration and a conductometric titration.
Figure 11:
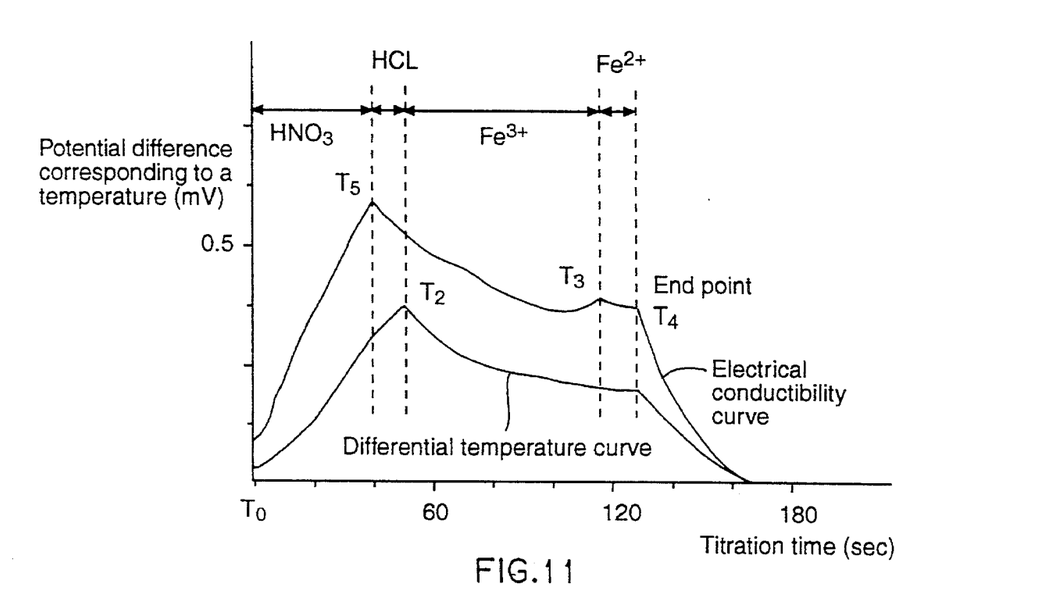

Japanese Laid Open Patent Application No. 62-2144 describes results of a thermometric titration for which the procedure had been known prior to the filing date of the afore-said Application No. 62-2144. In this thermometric titration, an aqueous solution of sodium hydroxide was used as a titrant, and an increasing amount of this titrant was added to a titrate in which nitric acid, hydrofluoric acid and ferric ions were known to coexist. Since nitric acid is a stronger acid and hydrofluoric acid is a weaker acid, a titration for determining the concentration of nitric acid naturally reaches an end point first, and a titration For determining the concentration of hydrofluoric acid reaches an end point next. On the other hand, hydrofluoric acid and nitric acid, both being relatively strong acids, do not vary from each other in reaching an end point so remarkably as a strong acid and a weak acid do from each other. Yet it is a known fact that respective end-point peaks of hydrofluoric acid and nitric acids vary from each other. Furthermore, as the titrant (sodium Hydroxide) is titrated, ferric ions ($Fe^{3+}$) and ferrous ions ($Fe^{3+}$) react with the titrant (sodium hydroxide) to form iron hydroxide which precipitates. However, solubility products by each of these ions in a same acid solution differ from each other, as a result, ferric ions ($Fe^{3+}$) precipitating earlier than ferrous ions ($Fe^{2+}$). This is depicted in FIGS. 10 and 11 (of the present specification) where the end points of respective ferric ions ($Fe^{3+}$) and ferrous ions ($Fe^{2+}$) vary from each other. In this way, the reaction on the titrant occurred in the order of nitric acid and hydrofluofic acid, and further in the order of ferric ions ($Fe^{3+}$) and ferrous ions ($Fe^{2+}$).

The prior art thermometric titration is such that, at the moment when a titration for determining the concentration of one kind of acid radicals or ions reaches an end point, a titration for determining the concentration of another kind of acid radicals or ions begins. There is little difference between the gradient of a line obtained from the preceding titration and the gradient of a line obtained from the succeeding titration. Consequently it is difficult to ascertain an end point of each titration which should appear as a point of intersection of the above-mentioned two lines.

The invention described in the Japanese Laid Open Patent Application No. 62-2144 was an attempt at overcoming the aforementioned difficulty of the prior art thermometric titration. A feature of this invention is the provision of a first temperature sensor capable of making a quick response to a temperature change and a second temperature sensor making a slow response to a temperature change. The difference between the output taken from the first temperature sensor and the output taken from the second temperature sensor was plotted on an ordinate against time on an abscissa. A differential temperature curve thus obtained has a clear point of inflection when an endothermic reaction is immediately followed by an exothermic reaction or vice versa in a series of chemical reactions which take place between the ingredients of the titrant and those of the titrate in the order named above.

However, when an endothermic reaction is immediately followed by another endothermic reaction or when an exothermic reaction is immediately followed by another exothermic reaction, it remains difficult to ascertain an end point which should exist between two reactions.

SUMMARY OF THE INVENTION

A primary object of the present invention is to provide a method of analyzing a solution in which a thermometric titration and a conductometric titration are used complementarily so that an end point which is hardly ascertained by one method of titration may be ascertained by the other method.

In order that the above-mentioned object, together with others as will hereinafter appear, may be attainable, the present invention consists generally in the steps of: providing a solution containing at least two of plural kinds of known free acids and ions, said known free acids and ions being different from each other in temperature changes and conductivity changes which are to occur in response to a titrant; placing in said solution a differential temperature sensor and an electrical conductivity sensor; adding to said solution at a constant rate a titrant which chemically acts upon said known free acids and ions to cause a thermometric titration and a conductometric titration thereof; recording during said thermometric titration and said conductometric titration differential temperature values and electric conductivity values respectively obtained substantially simultaneously from said differential temperature sensor and said electrical conductivity sensor; generating from respective recorded values a differential temperature curve and an electric conductivity curve; finding peak values on said electric conductivity curve and peak values on said differential temperature curve; measuring a length of time required for adding an increasing amount of said titrant until an point is reached, as indicated by each of said peak values; and finding a quantity of said titrant added during said length of time so as so obtain the concentration of free acids in said solution.

In accordance with the present invention, each end point has substantially even degree of articulation because of a thermometric titration and a conductometric titration used complementarily so that an end point which is hardly ascertained by one method of titration may be ascertained by the other method.

ADDITIONAL DISCLOSURE OF THE INVENTION

Figure 1:
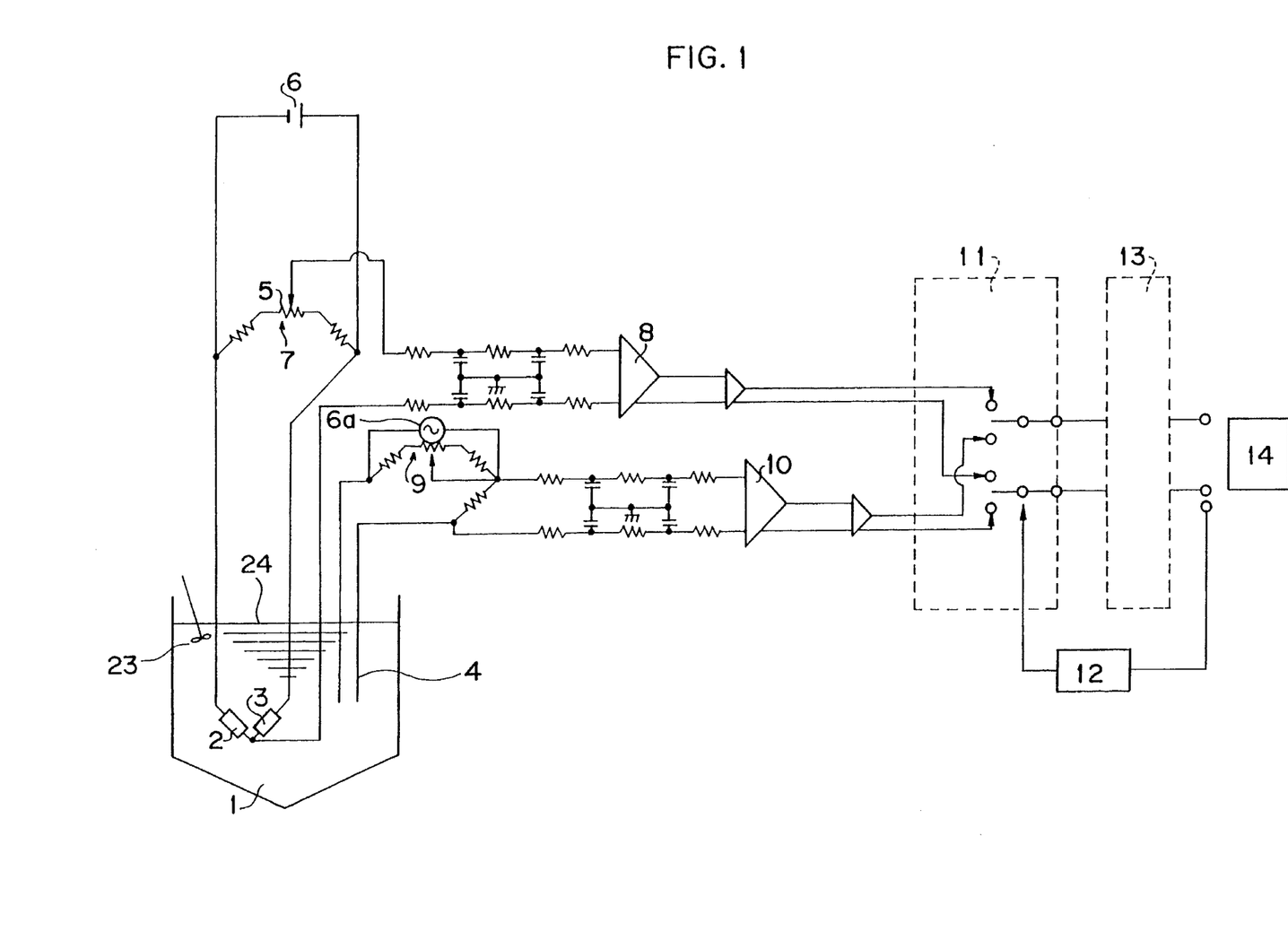
FIG. 1 shows a construction of a detecting portion for carrying out the thermometric titration and the measurement of electrical conductivity in an apparatus according to one preferred embodiment of the present invention.

The temperature-change and the electrical conductivity-change, which are basic ideas of the present invention, are described with reference to FIG. 1.

As to the temperature-change of the reaction solution, the titration time in a reaction tank (1) is short and said reaction tank (1) is held within an insulating system, so that it is hardly required to take the going in and out of heat other than the reaction heat into consideration. A pair of heat-sensitive resistance elements (2),(3) shown in FIG. 1 form an element for putting a first mode into practice, that is a differential temperature-detecting portion, adapted to have a difference in thermal response speed so as to detect the temperature-change due to the chemical reactions of dissolved ions with high sensitivity in the titration. In a temperature-detecting portion of said heat-sensitive resistance elements (2),(3), a difference in indicated temperature $\Delta T = T_1 - T_2$ resulting from an endothermic phenomenon or an exothermic phenomenon generated by the chemical reaction within an appointed short time (about 10 to 30 msec) in the reaction tank (1) is detected ($T_1$—an indicated temperature value of the heat-sensitive resistance element having a faster thermal response speed, $T_2$—an indicated temperature value of the heat-sensitive resistance element having a slower thermal response speed). If such detecting method is used, a temperature-change curve is apparently a primary differential curve. Hereinafter the method of detecting this temperature difference is referred to as the indication difference method. The temperature-change curve obtained by this indication difference method responds sharply to the smallest temperature-change. Since a change of electric resistance caused by a temperature in this indication difference method is very small, a signal is converted into an electric current by the unbalance of a bridge circuit (7) including a direct current-stabilizing power source (6) and then converted into a signal of voltage gradient dE/dt (dE: voltage-change; dt: very small time) through an amplifier circuit (8) followed by being taken in a computer (14) through a detector-changing over circuit (11), a changing over signal-generating portion (12) and an A/D convertor circuit (13) to be an object of the operation and control.

On the other hand, the electrical conductivity-change curve is obtained from a change of electrical conductivity in the solution with the lapse of time and the electrical conductivity is detected by means of an electrical conductivity sensor (4) provided with a pair of electrodes.

Figure 2:
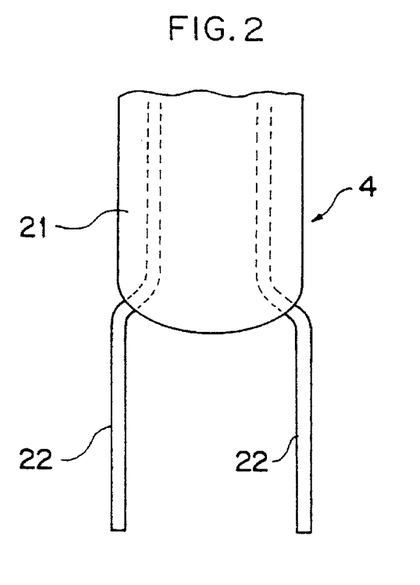
FIG. 2 is an enlarged front view showing an electrical conductivity sensor shown in Fig. 1.
Figure 3:
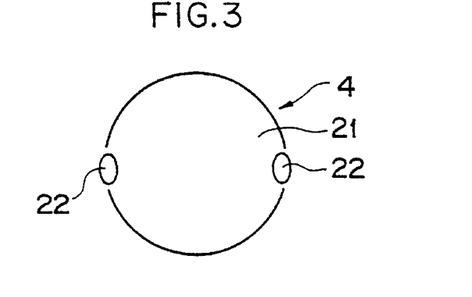
FIG. 3 is a bottom view showing the sensor shown in FIG. 2.
Figure 4:
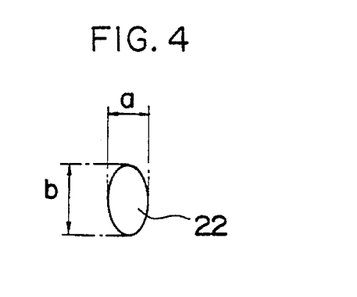
FIG. 4 is a diagram showing a sectional shape of an electrode in the sensor shown in FIGS. 2, 3.

Said electrical conductivity sensor (2) is detailedly shown in FIGS. 2 to 4. Reference numeral (21) designates a cylindrical supporting member formed of chemically stable resins. Reference numeral (22) designates a pair of electrodes passing through said supporting member (21) in the longitudinal direction and projecting outward from the supporting member (21) at a pointed end portion thereof. Said pair of electrodes (22) are formed of platinum electrodes disposed at an appointed interval therebetween and have an elliptical or non-circular section so that a ratio of the transversal diameter (a) to the conjugate axis (b) a:b may be 0.5:1.0 to 0.8:1.0. This sectional shape is uniform from the portion of the supporting member (21) to the pointed end of the electrodes (22).

A stirrer (23) is provided within the reaction tank (1) to stir a sample solution (24). If bubbles, which are generated in the stirring operation, and floating matters, which are produced in the titration reaction, are adhered to a surface of the electrodes (22), a surface area of the electrodes is changed, whereby the result of measurement is influenced in the form of the fluctuation of the indicated value of electrical conductivity and noises. In order to prevent foreign matters from adhering to the surface of the electrodes, it is sufficient to strongly stir but the strong stirring enhances the introduction of bubbles into the sample solution (24), whereby it is difficult to obtain stabilized data of measurement. On the contrary, if the elliptical section as shown in Figs.2 to 4 is used, the adherence of foreign matters to the surface of the electrodes (22) can be prevented even by weakly stirring.

Figure 5:
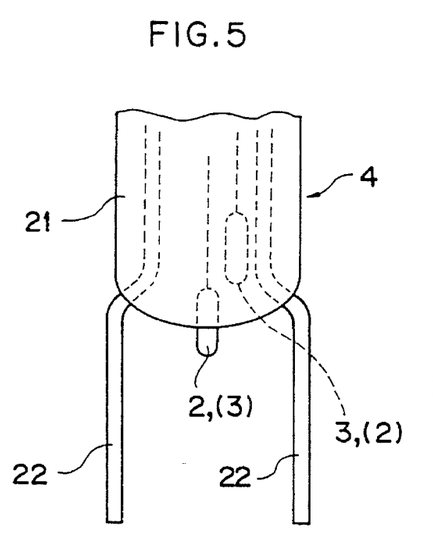
FIG. 5 is a front view showing the sensor integrally comprising a temperature-sensitive resistance element and the electrical conductivity sensor shown in FIG. 1.
Figure 6:
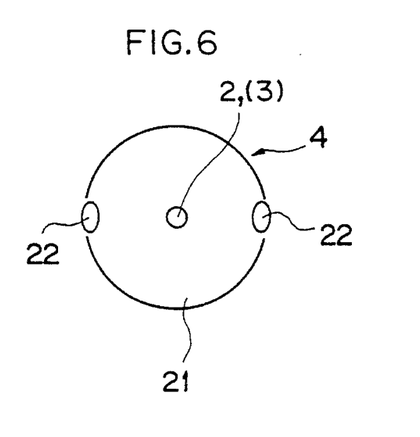
FIG. 6 is a bottom view showing the sensor shown in FIG. 5.

A differential temperature sensor can be integrated with the electrical conductivity sensor (4), as shown in FIGS. 5, 6. Measured values under the same one condition in the reaction tank (1) can be obtained without being accompanied by a substantial time lag by housing the heat-sensitive resistance elements (2), (3) in the supporting member (21), as shown in FIGS. 5, 6. As a result, a time lag in the analysis of data can be reduced to improve the accuracy. Also the heat-sensitive resistance elements (2), (3) have an elliptical section in the same manner as the electrodes (22) to increase the stability of measured values.

With the electrodes having an elliptical section shown in FIGS. 2 to 6, in the general system, in which electrodes are disposed within a titration-reaction tank and an insoluble dispersoid is formed within the reaction tank according to a kind of titrating solution used in dependence upon substances contained in the sample solution, the adherence of the reaction products to a surface of the electrodes can be effectively prevented.

A signal obtained by the use of the electrodes (22) having such the special shape catches the electrical conductivity-change in the form of a voltage-change, so that it is converted into an electric current by the unbalance of the bridge circuit (9) including an alternating-current power source (6a) for use in the measurement of electrical conductivity therein and then converted into a signal of voltage gradient dE/dt (dE: voltage-change; dt: very small time) through the amplifier circuit (10) followed by being taken in the computer (14) through the detector-changing over circuit (11), the changing over signal-generating portion (12) and the A/D convertor circuit (13) to be operated and controlled. In the above described manner, the electrical conductivity change can be continuously detected by the second mode from the start of the titration until the completion of the chemical reaction in the reaction tank (1) to obtain the electrical conductivity curve for the whole chemical reaction. Hereinafter this mode is referred to as the electrical conductivity-change method.

The respective change curves obtained by the indication difference method and the electrical conductivity-change method are stocked in the computer (12) time-sequentially and operated to determine the end point of the reaction. Whereupon, both change curves are analyzed at once to determine various kinds of factor, such as concentration of every solute ionic ingredient and total quantity of acids, in the sample solution in which the chemical reaction has been brought about.

An apparatus, in which two detecting methods and detecting mechanisms—said indication difference method and said electrical conductivity-change method—are incorporated into the continuous elution line, and a method of operating said apparatus are below roughly described.

Figure 7:
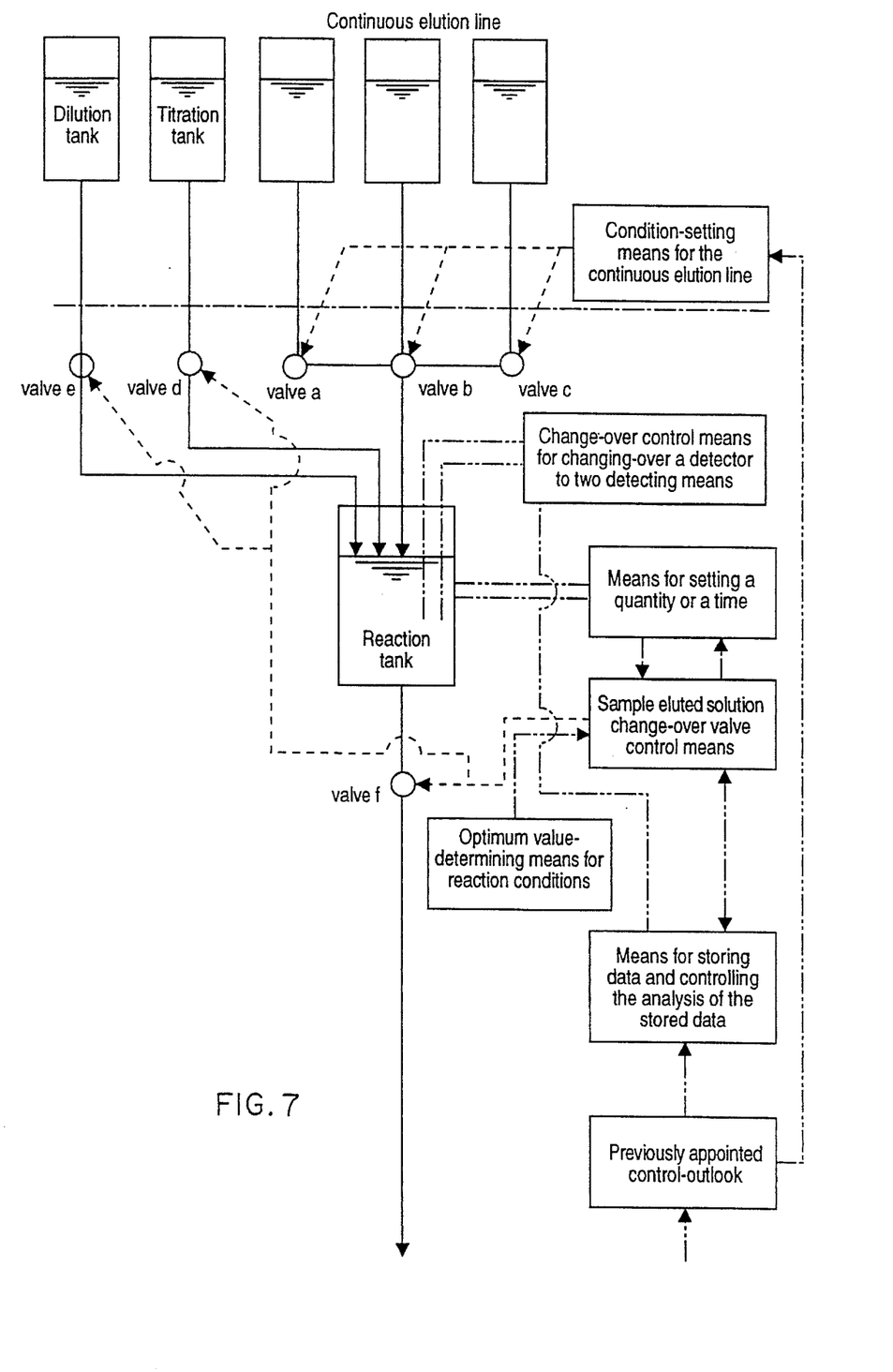
FIG. 7 is a rough block diagram showing a basic control device according to the present invention.

With this apparatus, a previously set appointed quantity of the solution eluted from the continuous elution line, in which known kinds of ion are contained, is automatically introduced into the reaction tank for every appointed quantity of elution or appointed time and the titrating solution is continuously poured into said reaction tank at a constant rate to automatically and continuously separate and quantitatively determine many kinds of ionic ingredient dissolved in the eluted solution within a short time. Its basic construction is described with reference to Fig. 7. As shown in FIG. 7, the appointed quantity of eluted solution is introduced into the reaction tank by opening any one of valves (a), (b), (c) by means of at least one series of "continuous elution line condition-setting means", a valve (d) of the titration tank being opened by "sampling-drainage change over valve-controlling means" and "quantity or time-setting means" to automatically and continuously add the previously prepared titrating solution to the eluted solution at the constant rate, thereby brining about the chemical reaction, with the very small temperature-change and electrical conductivity-change resulting from the chemical reaction being continuously detected by two characteristic signal values to analyze the reaction. In order to conduct this analysis and control operation of the present apparatus, "data-storing and analytical operation-controlling means" is provided. This analytical means is provided with means for determining the total quantity of acids and the like of the continuous elution line.

According to the present invention, the temperature-change and electrical conductivity-change of the reaction liquid can be continuously detected to separate and quantitatively determine the ionic ingredients dissolved. In case of need, a program for controlling the quantity of sample solution to be introduced into the reaction tank or a program of a large number of "continuous elution line condition-setting means", a program of "sampling-drainage change over valve-controlling means " opening a valve (f) of the reaction tank and a driving mechanism may be adopted. For example, in the case where it is not necessary to measure the temperature-change and the electrical conductivity-change within the reaction tank, it is sufficient to put "a previously appointed control prospect" in the computer and drain the solution from the reaction tank by controlling the valve (f). In addition, for example in the case where the concentration of the ingredients in the solution is extraordinarily high so as not to be able to sufficiently stir, "optimum reaction condition-establishing means" capable of adjusting the reaction conditions to the optimum values by opening a valve (e) of a diluent solution tank to add a diluent solution to the sample solution may be provided. Furthermore, a digital computer is suitably used for the operation and control in the present apparatus but also an analog operating controller may be used.

DESCRIPTION OF THE PREFERRED EMBODIMENTS

The preferred embodiments of the apparatus according to the present invention are concretely described below with reference to FIG. 8.

Figure 8:
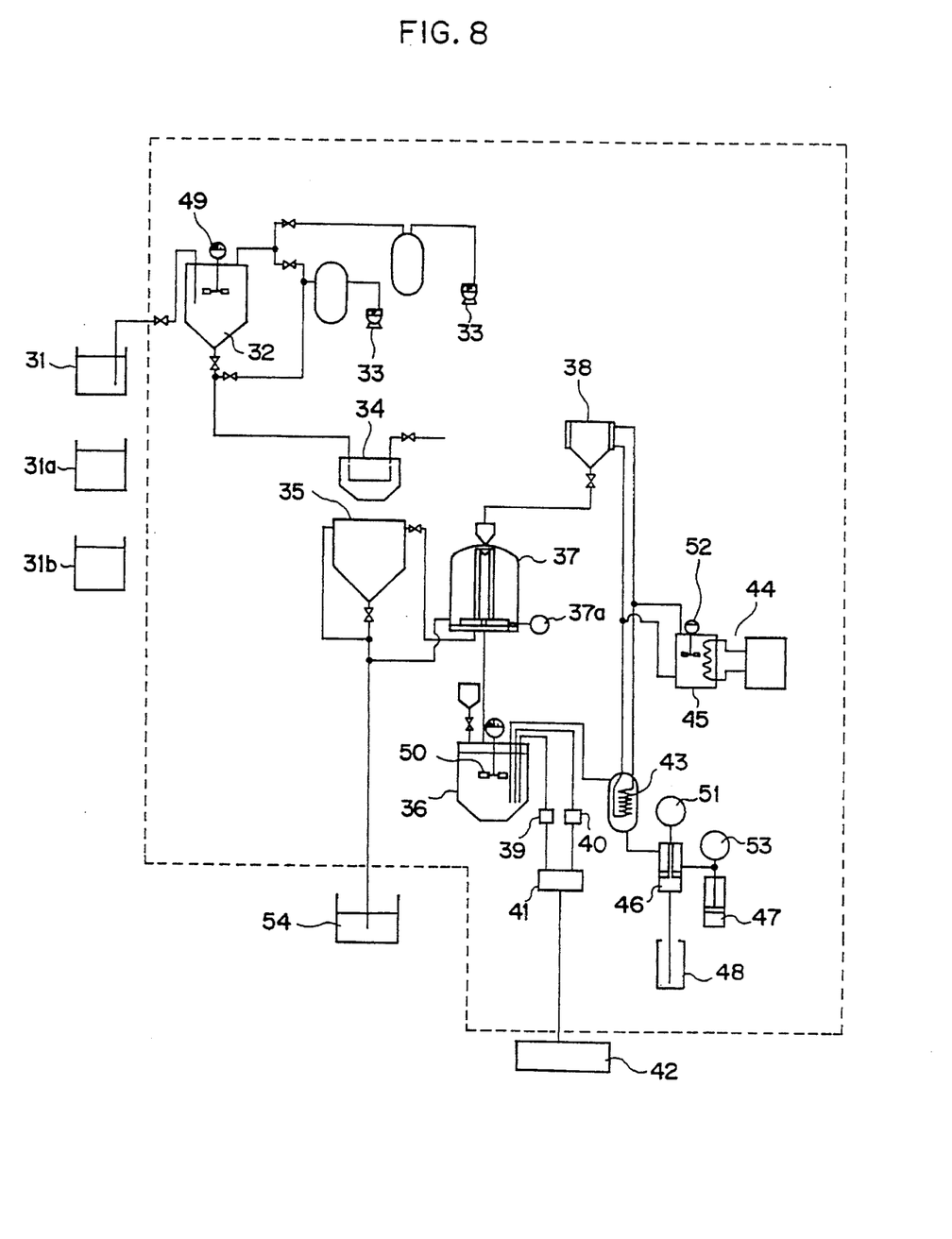
FIG. 8 shows a device for carrying out the temperature titration and the measurement of electrical conductivity.

In addition, FIG. 8 shows one preferred embodiment of the present invention merely for illustration and accordingly, the present invention is not limited by the preferred embodiments. The apparatus shown in the drawing according to the preferred embodiments is described with the case where it is used for the partition quantitative determination of many kinds of dissolved ionic ingredient as an example.

EXAMPLE 1

Referring to FIG. 8, a sample pickling solution comprising $HNO_3$ and HF is introduced into a sample tank (32) from a bath tank (31), in which wire materials made of stainless alloys have been subjected to the pickling, an appointed quantity of the sample pickling solution being automatically taken out from said sample tank (32) by means of a pump (33) to be transferred to a cooling tank (34), where very small floating matters are filtrated, and the resulting filtrate being put in a filtration tank (35). Then, the filtrated sample solution is introduced into a measuring tank (37) to send a sample of 0.5 cc together with 10 cc of a diluent water (38), whose temperature has been previously controlled in a thermostatic oven (45), to a reaction tank (36) having an internal capacity of 18 cc with a meter (37a) of said measuring tank (37) measuring said diluent water (38). Said reaction tank (36) is formed of corrosion resistant materials such as polytetrafluoroethylene. The reaction vessel (36) is provided with a stirrer (50) formed of polytetrafluoroethylene disposed therewithin and insulated so as to make the heat exchange with the outside minimum.

After the lapse of about 80 seconds since the introduction of the diluent solution into the reaction tank (36), a previously prepared 2 N-sodium hydroxide titrating solution is begun to be poured into the reaction tank (36) through a titrating solution-supply portion (46) from a tank (48) by means of a constant-quantity filling pump (47) to bring about a neutralization reaction within the reaction tank (36). A state of reaction solution changing with the lapse of time resulting from the neutralization reaction within the reaction tank (36) is continuously converted into signals in a temperature-detecting portion (39) and an electrical conductivity-detecting portion of the respective sensors in the indication difference method and the electrical conductivity-change method and the resulting signals are put in a computer (42) through a signal conversion circuit (41) to compile and analyze data.

Referring to FIG. 8 again, reference numeral (43) designates a temperature-controlling pipe of the titrating solution communicated with a thermostatic tank (45). Reference numeral (44) designates a temperature-regulating portion of said thermostatic tank (45). Reference numerals (51), (53) designate a driving motor for driving the titrating solution-supply portion (46) and the constant-quantity filling pump (47), respectively. Reference numerals (49), (52) designate a stirrer for the sample tank (32) and the thermostatic tank (45), respectively. Reference numeral (54) designates a drain-receiving tank for the solution stocked for measuring the sample.

If the constant-quantity feeding of the titrating 2 N-aqueous solution of sodium hydroxide is conducted at such a rate that the reaction may arrive at the end point within about 120 to 180 seconds, the thermometric-titration and the electrical conductivity-change can be easily analyzed. In addition, a quantity of the solution used for the titration about 1/10 to 1/20 times that of the diluent solution is optimum.

Figure 9:
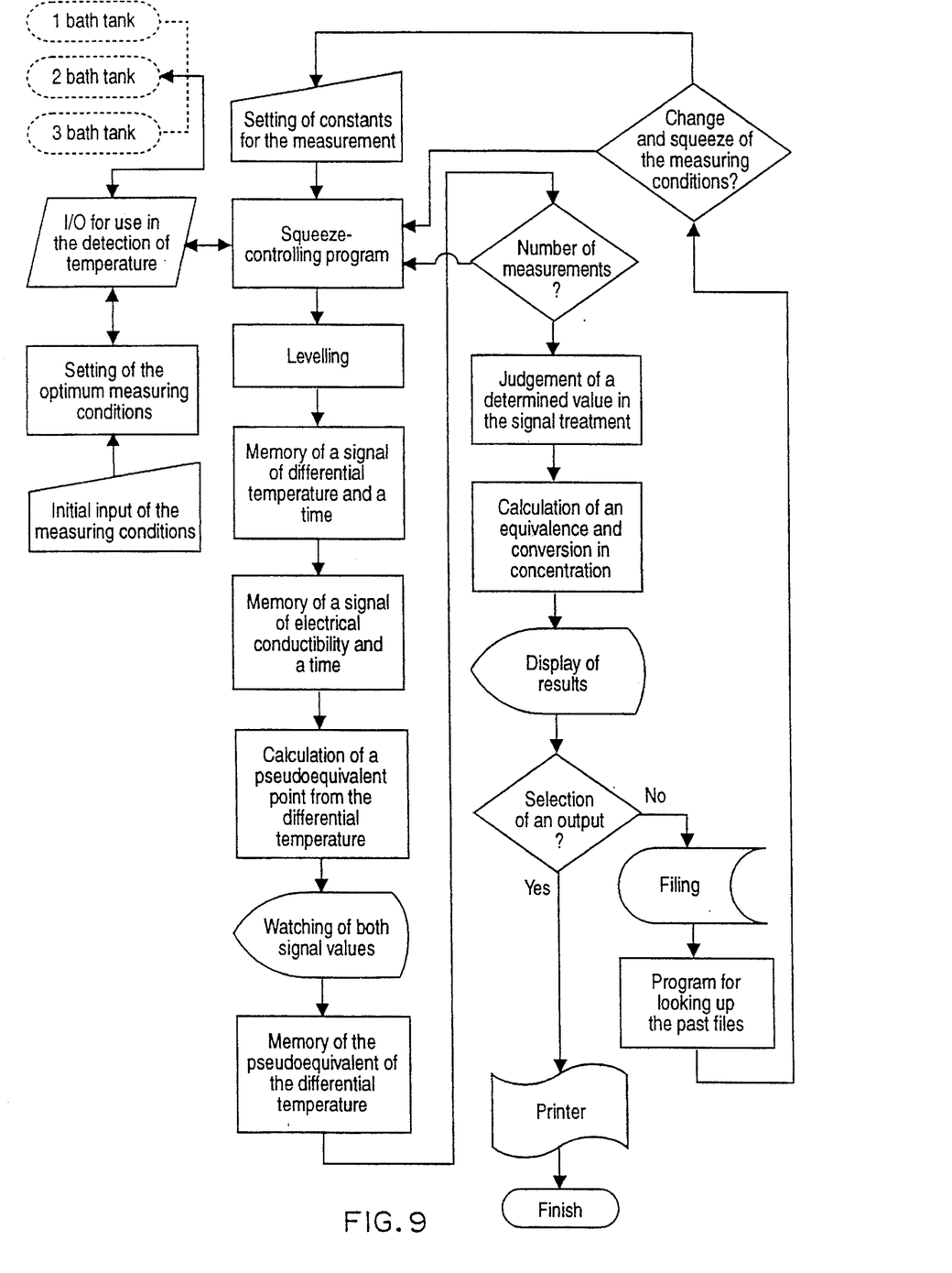
FIG. 9 is a flow chart corresponding to the device shown in FIG. 8.

In order to still further detailedly describe the preferred embodiments of the present invention, a flow chart of programs shown in FIG. 9 relating to the apparatus and mechanism shown in FIG. 8 is described below.

In the process according to the present invention, the initial values of constants for the measurement and control as well as the measuring conditions, in particular their optimum conditions, are put in from outside, the sample eluted solution being introduced into the reaction tank from the previously appointed bath tank, the reaction reagent being added to the sample eluted solution to bring about the chemical reaction, and the temperature-change and ionic dissociation characteristics in the process of said chemical reaction being detected by two methods—the indication difference method and the electrical conductivity-change method.

The detection of these two signals is put into practice from the I/O program of the temperature-detection and electrical conductivity-detection through the control-starting program.

In the detection of these two signals, in order to improve the S/N ratio, the levelling treatment is carried out and when the S/N ratio reaches the appointed value, the respective signals and the respective times at that time being determined, and then they are memorized in the form of the respective signal values corresponding thereto.

In this flow, the positions of the equivalent points of the reactions brought about in the respective reaction steps are calculated by the supplementary program for looking for the point of inflection from the temperature-change curve obtained by the indication difference method.

These two signal-change curves are continuously watched on a CRT of a terminal of the computer until the measurement reaches the end point and the measured points are recorded. After the completion of the measurement, the signal values of the temperature-change and the electrical conductivity-change obtained by two methods are taken out from the memory to be automatically processed by an editing program, for example an operation of marking the point of inflection in the curve is automatically carried out. The results of the thermometric-titration and the measurement of electrical conductivity are shown in FIG. 10. It is judged that the largest point of inflection seen first from a titration-starting point of time ($T_0$) on the electrical conductivity-change curve is an equivalent point ($T_1$) of a nitrate group and the largest point of inflection ($T_2$) seen on the differential temperature-change curve is a synthetic equivalent point of free acids. Subsequently, a point of inflection ($T_3$) seen on the electrical conductivity-change curve is determined. This ($T_3$) is an equivalent point of metallic salts and ($T_4$) is determined additionally. As to the end point of the reaction, the largest and last point of inflection seen on the electrical conductivity-change curve after the point of time when no point of inflection can be seen on the differential temperature-change curve is regarded as the end point of the reaction. The end point ($T_4$) of the whole chemical reaction system is determined from the electrical conductivity-change curve in the above described manner to determine the total quantity of acids, and additionally the respective compositional ratios are determined from the respective pseudoequivalent points (or peak valves on the differential temperature curve), which have been previously determined by the indication difference method, and the points of inflection on the electrical conductivity-change curve are determined by the supplementary program.

On the basis of the analysis of the above described points of inflection, the compositions of the respective ingredients are determined as follows, that is a quantity of a free nitric acid group is calculated by $(T_1)-(T_0)$, a quantity of fluoric acid group being calculated by $(T_2)-(T_1)$, a quantity of 3-valence metallic ions being calculated by $(T_3)-(T_2)$, and a quantity of 2-valence metallic ions being calculated by $(T_4)-(T_3)$. Accordingly, the total quantity of free acid groups is determined by $(T_2)-(T_0)$ and the total quantity of metallic ingredients is determined by $(T_4)-(T_2)$.

After the completion of the analysis of the chemical reaction, the results are printed by means of a printer or put in a memory medium for filing. In addition, it is possible also to reproduce the control by looking up the past files in case of need. Besides, in order to cope with the changes of the measuring conditions, a squeezible supplementary program is provided.

According to the present preferred embodiment, the temperature-change and the electrical conductivity-change brought about in the reaction tank can be caught sharply and in high accuracy by obtaining two kinds of change curve by the use of the indication difference method together with the electrical conductivity-change method. That is to say, since the differential temperature curve and the electrical conductivity curve show sharp changes at the equivalent points in the respective steps of the reaction, the existence of the equivalent points can be surely shown and the quantity of the titrating solution consumed until the respective equivalent points can be shown in high accuracy.

The indication difference method can sharply detect the equivalences of the respective free acids. On the other hand, the electrical conductivity-change method shows $HNO_3$, 2-valence metals and the change of the end point of the reaction more clearly than the indication difference method.

Even the sample solution, which is difficult to judge by merely the differential temperature curve, can be appropriately and surely detected and judged by synergistically using these two detecting methods to investigate also the electrical conductivity curve. In addition, the detecting method can be simplified. The influences by heat coming from the outside during the reaction and the change of the heat-sensitive resistance element in detection sensitivity by the floating matters formed by the reaction are compensated by measuring the electrical resistance curve.

The total quantity of free acids, the quantity of the free nitric acid ion and the quantity of the free fluorine ion were calculated from the points of inflection obtained by the indication difference method and the points of inflection obtained by the electrical conductivity-change method of the curves shown in FIG. 10 and the concentrations of ferrous ion and ferric ion were calculated from the points of inflection obtained by the electrical conductivity-change method by means of the computer.

The concentration of each kind of free acids or ions was determined by measuring a length of time required for adding at the constant rate an increasing amount of the titrant until an end point was reached, as indicated by each of the peak values, and by finding a quantity of the titrant added during the abovementioned length of time.

The reliability of the kinds and concentrations of the respective eluted ionic ingredients determined by the present method and apparatus was confirmed by putting the standard solutions of the respective ions in the same one apparatus, pouring the titrating solution into said respective standard solutions to make the chemical reactions progress, obtaining the differential temperature curve and the electrical conductivity curve, and analyzing said curves.

As a result, it was found that all kinds of ionic ingredient in the present preferred embodiment of the present invention were shown on the graphs and errors of measurement for the respective ion concentrations were held within ±2.5 %. Thus, it was confirmed that the respective ionic ingredients in the solution eluted from the metal pickled could be accurately identified and quantitatively determined by the method and apparatus according to the present invention. Table 1 shows the titrating conditions and the measured results according to the method disclosed in the above described Japanese Patent Application Laid-Open No. Sho 62-2144 and the method of the present invention.

TABLE 1

| Temperature within the reaction tank | Temperature of alkali to be poured | Free nitric acid (N) | | Free HF (N) | | Fe(3+) (N) | | Fe(2+) (N) | | Total acid (N) | |
|---|---|---|---|---|---|---|---|---|---|---|---|
| | | Theoretical | Measured | Theoretical | Measured | Theoretical | Measured | Theoretical | Measured | Theoretical | Measured |
| Method according to Japanese Patent Application Laid-Open No. Sho 62-2144 | | | | | | | | | | | |
| 15° C. | 14.5° C. | 0.8 | 0.75 | 0.5 | 0.55 | 0.3 | 0.25 | 0.3 | 0.31 | 1.9 | 1.86 |
| 20° C. | 18° C. | 0.8 | 0.65 | 0.5 | 0.65 | 0.3 | 0.4 | 0.3 | 0.2 | 1.9 | 1.9 |
| 20 | 20 | 0.8 | 0.87 | 0.5 | 0.43 | 0.3 | 0.35 | 0.3 | 0.3 | 1.9 | 1.95 |
| 25 | 19 | 0.8 | 0.70 | 0.5 | 0.6 | 0.3 | 0.15 | 0.3 | 0.4 | 1.9 | 1.85 |
| Method according to the present invention | | | | | | | | | | | |
| 15° C. | 14.5° C. | 0.8 | 0.78 | 0.5 | 0.51 | 0.3 | 0.28 | 0.3 | 0.29 | 1.9 | 1.86 |
| 20° C. | 18° C. | 0.8 | 0.79 | 0.5 | 0.50 | 0.3 | 0.29 | 0.3 | 0.29 | 1.9 | 1.87 |
| 20 | 20 | 0.8 | 0.79 | 0.5 | 0.49 | 0.3 | 0.30 | 0.3 | 0.31 | 1.9 | 1.89 |
| 25 | 19 | 0.8 | 0.81 | 0.5 | 0.49 | 0.3 | 0.29 | 0.3 | 0.29 | 1.9 | 1.88 |

In addition, the present invention is superior also in the case where a mixture of compounds different in reaction heat and ionic dissociation characteristic is analyzed. Furthermore, even in the case where a mixture containing compounds, which are difficult to be dissociated, is analyzed, the partition is possible by making them coexist in the form of third substances, which easily form a complex, to generate a difference between the mixed substances if reaction speed.

EXAMPLE 2

A solution containing $HNO_3$ and $HCl$ eluted from a metal when pickled was analyzed by the method used in EXAMPLE 1.

As shown in FIG. 11, the detections of free acids, such as $HNO_3$ ($T_2$) and $HCl$ ($T_5$), and ferric ion ($T_3$) were possible.

What is claimed is:

1. A method of obtaining concentrations of free acids and ions in a solution, said solution being known beforehand to contain plural kinds of free acids and ions different from each other in temperature changes and conductivity changes which occur in response to a titrant, comprising the steps of:

a. preparing a solution containing at least two of plural kinds of known free acids and ions, said known free acids and ions being different from each other in temperature changes and conductivity changes which occur in response to a titrant;

b. placing in said solution a device integrally comprising a differential temperature sensor and an electrical conductivity sensor;

c. continuously adding to said solution, at a constant rate, a titrant which chemically reacts with said known free acids and ions, in order to cause a thermometric titration and a conductometric titration of said known free acids and ions;

d. recording during said thermometric titration and said conductometric titration, differential temperature values and electric conductivity values respectively obtained substantially simultaneously from said integral device comprising said differential temperature sensor and said electrical conductivity sensor which is placed in said solution;

e. generating from said respective recorded values a differential temperature curve and an electrical conductivity curve prepared by plotting said values with respect to time during which said titrant was added to said solution;

f. obtaining true peak values by identifying apparent peak values on one of said electrical conductivity curve or said differential temperature curve and then superposing said apparent peak values on the other of said curves for mutual compensation therebetween to obtain said true peak values;

g. measuring a length of time between any two adjacent pairs of said true peak values;

h. calculating a quantity of said titrant added to said solution during said length of time; and i. measuring the concentrations of said free acids and ions on the basis of said calculated quantity of said titrant.

2. The method as set forth in claim 1, wherein said differential temperature values are obtained by employing two heat-sensitive resistance elements having a substantially equal heat-sensitive resistance and having thermal response speeds different from each other.

3. A method of obtaining concentrations of free acids and ions in a solution, said solution being known beforehand to contain plural kinds of free acids and ions different from each other in temperature changes and conductivity changes which occur in response to a titrant, comprising the steps of:

a. preparing a solution containing at least two of plural kinds of known free acids and ions, said known free acids and ions being different from each other in temperature changes and conductivity changes which occur in response to a titrant;

b. continuously adding to said solution, at a constant rate, a titrant which chemically reacts with said known free acids and ions to cause a thermometric titration and a conductometric titration of said known free acids and ions;

c. generating during said thermometric titration and conductometric titration a differential temperature curve and an electrical conductivity curve from respective outputs from a device integrally comprising a differential temperature sensor and an electrical conductivity sensor placed in said solution;

d. obtaining true peak values by identifying apparent peak values on one of said electrical conductivity curve or said differential temperature curve and then superposing said apparent peak values on the other of said curves for mutual compensation therebetween to obtain said true peak values;

e. measuring a length of time between any two adjacent pairs of said true peak values;

f. calculating a quantity of said titrant added to said solution during said length of time; and g. measuring the concentrations of said free acids and ions on the basis of said calculated quantity of said titrant.

4. A method of obtaining concentrations of free acids and ions in a solution, said solution being known beforehand to contain plural kinds of free acids and ions different from each other in temperature changes and conductivity changes which occur in response to a titrant, comprising the steps of:

a. feeding into a reaction tank a solution containing at least two of plural kinds of known free acids and ions, said known free acids and ions being different from each other in temperature changes and conductivity changes which occur in response to a titrant;

b. adding to said solution while stirring, a diluent water of ten to twenty times of said solution in quantity, which is then allowed to stand for a certain length of time;

c. placing in said solution a device integrally comprising (1) a differential temperature sensor comprising a first bridge circuit including two heat-sensitive resistance elements each having a different thermal response speed and (2) an electrical conductivity sensor comprising a second bridge circuit different from said first bridge circuit;

d. continuously adding to said solution, at a constant rate, a titrant kept at the same temperature as said diluent water which chemically reacts with said known free acids and ions in order to conduct a thermometric titration and a conductometric titration of said solution;

e. generating a differential temperature curve and an electrical conductivity curve from differential temperature values and electrical conductivity values, respectively given substantially simultaneously from said first and second bridge circuits, during said thermometric and conductometric titrations;

f. finding apparent peak values on one of the differential temperature curve or the electrical conductivity curve, and then superposing said apparent values on the other of said curves for mutual compensation therebetween, to obtain true peak values;

g. measuring a length of time between any two adjacent pairs of said true peak values;

h. calculating a quantity of said titrant added to said solution during said length of time; and i. measuring the concentrations of said free acids and ions on the basis of said calculated quantity of said titrant.

* * * * *